United States Patent [19]

Nelson

[11] 4,430,502

[45] Feb. 7, 1984

[54] PYRIDINYL SUBSTITUTED BENZIMIDAZOLES AND QUINOXALINES

[75] Inventor: Norman A. Nelson, Galesburg, Mich.

[73] Assignee: The Upjohn Company, Kalamazoo, Mich.

[21] Appl. No.: 407,853

[22] Filed: Aug. 13, 1982

[51] Int. Cl.$^3$ ............... C07D 401/12; C07D 401/06; A61K 31/44
[52] U.S. Cl. .................................... 544/354; 546/271; 424/250; 424/263
[58] Field of Search ..................... 544/354; 546/271

[56] References Cited

U.S. PATENT DOCUMENTS

| | | | |
|---|---|---|---|
| 4,026,936 | 5/1977 | Lauer | 546/271 |
| 4,032,536 | 6/1977 | Raeymaekers et al. | |
| 4,112,224 | 9/1978 | Bundy | 542/426 |
| 4,259,338 | 3/1981 | Paioni et al. | 424/267 |
| 4,331,671 | 5/1982 | Lesher | 424/263 |
| 4,335,132 | 6/1982 | Lesher | 546/271 |

FOREIGN PATENT DOCUMENTS 2537837 of 0000 Fed. Rep. of Germany.
2039903A of 0000 United Kingdom.

OTHER PUBLICATIONS

D. Harris et al., Advances in Prostaglandin and Thromboxane Research, 6:437 (1980).
T. Miyamoto et al., Advances in Prostaglandin and Thromboxane Research, 6:443 (1980).
H. Tai et al., Advances in Prostaglandin and Thromboxane Research, 6:447 (1980).
Dol'nikov et al., Chem. Abs., vol. 76, 1972, 135663h.

*Primary Examiner*—Mark L. Berch
*Assistant Examiner*—C. Kalita
*Attorney, Agent, or Firm*—Lawrence T. Welch

[57] ABSTRACT

The present invention provides novel pyridinyl-benzimidazoles and quinoxalines which are useful as thromboxane $A_2$ ($TXA_2$) synthetase inhibitors and as such represent potent pharmacological agents.

7 Claims, No Drawings

PYRIDINYL SUBSTITUTED BENZIMIDAZOLES AND QUINOXALINES

BACKGROUND OF THE INVENTION

The present invention relates to novel compositions of matter. More particularly, the present invention relates to pyridinyl substituted benzimidazoles and quinoxalines and derivatives thereof. These compounds are potent thromboxane A$_2$ inhibitors and as such represent useful pharmacological agents.

Since the discovery that human platelets convert the prostaglandin endoperoxide (PGH$_2$) into a labile proaggregatory molecule known as thromboxane A$_2$ (TXA$_2$), researchers have sought compounds that could selectively inhibit the biological activity of TXA$_2$. This end may be achieved in two different ways: the synthesis of TXA$_2$ can be blocked by inhibiting the TXA$_2$ synthetase, or a compound could be a receptor level antagonist of TXA$_2$. As therapeutic agents, TXA$_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit TXA$_2$ synthetase. Id.

PRIOR ART

A number of TXA$_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromboxane Research, 6:443 (1980), and British patent application 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)phenyl phosphate, imidazoles, nordihydroguaiaretic acid, and 12L-hydroperoxy-5,8,10,14-eicosa-tetraenoic acid (HETE). As noted in the above named British patent specification, however, the inhibitory activity of these latter compounds on thromboxane synthetase is very weak making them unsatisfactory as practically effective medicines.

Tetrahydropyridinyl- and piperidinyl-substituted benzofurans are disclosed in U.S. Pat. No. 4,259,338 as psychopharmaceuticals and antidepressants. Similar compounds are disclosed in German Offenleggunschrift No. 2,537,837.

SUMMARY OF THE INVENTION

Surprisingly and unexpectedly it has been found that selective thromboxane synthetase inhibition may be achieved by employing a compound of the formula I or II
wherein Z$_1$ is
 (a) 4-pyridinyl,
 (b) 3-pyridinyl, or
 (c) 3-pyridinyl substituted by (C$_1$–C$_4$)alkyl;
wherein X$_1$ is
 (a) —(CH$_2$)$_n$—,
 (b) —O—,
 (c) —CH$_2$—O—, or
 (d) —O—CH$_2$—;
wherein Y$_1$ is —(CH$_2$)$_m$—R$_7$;
wherein R$_1$ is hydrogen, a pharmacologically acceptable cation, (C$_1$–C$_{12}$) alkyl, (C$_3$–C$_{10}$) cycloalkyl, (C$_7$–C$_{12}$) aralkyl, phenyl, phenyl mono-, di-, or trisubstituted by chloro, or (C$_1$–C$_3$) alkyl, or phenyl para-substituted by
 (a) —NHCO—R$_{25}$,
 (b) —O—CO—R$_{26}$,
 (c) —CO—R$_{24}$,
 (d) —O—CO—(p—Ph)—R$_{27}$, or
 (e) —CH=N—NH—CO—NH$_2$,
wherein R$_{24}$ is phenyl or acetamidophenyl, R$_{25}$ is methyl, phenyl, acetamidophenyl, benzamidophenyl, or amino, R$_{26}$ is methyl, phenyl, amino or methoxy; and R$_{27}$ is hydrogen or acetamido, and wherein —(p—Ph) is 1,4-phenylene;
wherein R$_7$ is
 (a) hydrogen,
 (b) —CH$_2$OH,
 (c) —CHO, or
 (d) —COOR$_1$;
wherein m is an integer of from 0 to 4, inclusive; and wherein n is an integer of from 1 to 3, inclusive;
including, pharmacologically acceptable acid addition salts thereof and the tautomeric forms thereof.

Thus, the present invention provides benzimidazoles of the formula I and quinoxalines of the formula II and IIa. Note that the compound of formula II exists as a tautomer with the formula IIa compound. Both forms are within the scope of this invention.

The carbon atom content of various hydrocarbon-containing moieties is indicated by a prefix designating the minimum and maximum number of carbon atoms in the moiety, i.e., the prefix (C$_i$–C$_j$) indicates a moiety of the integer "i" to the integer "j" carbon atoms, inclusive. Thus (C$_1$–C$_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when R$_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine,
4-ethylmorpholine,
1-isopropylpyrrolidine,
2-methylpyrrolidine,
1,4-dimethylpiperazine,
2-methylpiperidine, and the like, as well as amines containing water-solubilizing or hydrophilic groups, e.g., mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine, and the like. Further useful amine salts are the basic amino acid salts, e.g., lysine and
arginine.

Examples of suitable pharmacologically acceptable quaternary ammonium cations are tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as benzimidazoles (the formula II compounds) and quinoxalines (the formula III compounds), using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention were tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

Using this test system, one compound, 5-(3-pyridinylmethyl)-benzimidazole (Example 3), has been shown to be the most effective in inhibiting $TXA_2$ formation. This compound has an approximate $ED_{50}$ in this system of 100 ng/ml.

The novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg to about 500 µg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification 2,039,903A).

For a general discussion of the utility of $TXA_2$ synthetase inhibitors which increase endogenous prostacyclin, see, Aiken, et al. J. Pharmacol, Exp. Ther., d219:299 (1981).

The compounds of the present invention are prepared by the methods depicted in Charts A and B.

The benzimidazoles of the formula I are prepared by the method of Chart A. Referring to Chart A, a compound of the formula A-1 is nitrated by procedures well known in the art, e.g., treatment with nitric and sulfuric acids, to yield the formula A-2 compound. Milder nitration conditions, e.g., less sulfuric acid, are used when $X_1$ is —$CH_2$—O— or —O—. Compounds of the formula A-1 are known in the art and are available commercially or may be prepared by known means. Conversion of the formula A-2 compounds to the formula A-3 compound is accomplished by catalytic hydrogen (using, e.g., a palladium or nickel catalyst) or by chemical reduction (using, e.g., zinc dust or iron). Reaction of the formula A-3 compound thus formed with acetic anhydride (or other acid chloride or anhydride) yields the formula A-4 protected intermediate wherein —NHAc represents an acyl protecting group. This compound is nitrated using known means (e.g. treatment with nitric acid as described in preparation 2) to yield the formula A-5 compound. The acyl protecting group is removed by mild acidic hydrolysis and the addition of base liberates the formula A-6 compound. Reduction of the nitro group as described above yields the formula A-7 diamino compound. This formula A-7 diamino compound is sensitive to air oxidation and is thus advantageously used under a nitrogen or argon atmosphere. This formula A-7 diamino compound is used to prepare final products of the formula A-8, A-9, A-10, and A-11, wherein $Y_2$ is hydrogen, —$(CH_2)_{n-1}$—$CH_2OH$, or —$(CH_2)_{n-1}$—COOH. The methods used to prepare these compounds are set forth, for example, in The Chemistry of Heterocyclic Compounds, Vol. 40, part 1, titled "Benzimidazoles and Congeneric Tricyclic Compounds" (John Wiley and Sons 1981). Synthesis of the formula A-8 and A-11 compounds is more particularly described in M. A. Philips, J. Chem. Soc. 2393 (1928); Bistrzycki, et al., Ber. 45:3483(1912); and R. Copeland, et al., J. Am. Chem. Soc. 65:1073 (1943).

Compounds of the formula A-8 wherein $Y_2$ is hydrogen are prepared by treating the formula A-7 compound with formic acid (see, e.g., C. Haley, et al., J. Chem. Soc. 3155 (1951)). An alternate, though less desirable, method is described in Example 3.

Compounds of the formula A-8 wherein $Y_2$ is —$(CH_2)_{n-1}CH_2OH$ are prepared by heating the formula A-7 compound with an appropriate hydroxy acid (or a lactone of the hydroxy acid) and a mineral acid, as described more fully in Example 1.

Compounds of the formula A-8 wherein $Y_2$ is —$(CH_2)_{n-1}$—COOH are prepared by heating the formula A-7 compound with an appropirate dicarboxylic acid (or cyclic anhydride) in a solvent such as dioxane for several hours. This method cannot be used to generate the formula A-11 compound. The formula A-11 compound is prepared by oxidation of the formula A-8 compound wherein $Y_1$ is —$(CH_2)_0$—$CH_2OH$ as set forth in Example 4.

Compounds of the formula A-9 are prepared by oxidation of the corresponding primary alcohol as set forth in Example 2.

Compounds of the formula A-10 are prepared by oxidation of the corresponding formula A-8 primary alcohol by methods well known in the art for conversion of alcohols to aldehydes, e.g. Collins oxidation (using a chromium trioxide-pyridine complex) or Pfitzner-Moffett oxidation.

The quinoxalines of the formulas II and IIa are prepared by the method depicted in Chart B. A compound of the formula B-1 (which corresponds to formula A-7 and is prepared as depicted therein) is heated with an oxalic acid or an ester thereof to yield the formula B-2 and B-3 Tautomers. This is described more fully in Example 5.

The pharmacologically acceptable salts, phenacyl esters, amides, and the like corresponding to compounds of the present invention wherein $R_7$ is —COOH are prepared by means well known in the art, see e.g., U.S. Pat. Nos. 4,292,445 and 4,172,206, and Example 4.

Preparation of the various other benzimidazoles and quinoxaline derivatives within the scope of this invention are prepared by analogous procedures well known in the art.

Certain compounds of the present invention are preferred. Thus, compounds of the formula I, wherein $Y_1$ is —$(CH_2)_mR_7$ (wherein m is zero), $X_1$ is —$(CH_2)_n$— (wherein n is one) or —O—, $Z_1$ is 3-pyridinyl, and $R_7$ is $COOR_1$, hydrogen, —$CH_2OH$, and —CHO are preferred. Compounds of this latter class wherein $X_1$ is —$CH_2$— and $R_7$ is hydrogen are more preferred. Thus, 5-(3-pyridinylmethyl)benzimidazole is the most preferred compound of this invention.

DESCRIPTION OF THE PREFERRED EMBODIMENTS

The operation of the present invention is seen more fully by the examples given below.

Preparation 1

N-[4-(3-Pyridinylmethyl)phenyl]acetamide

Refer to Chart A (conversion of A-3 to A-4).

To a fine suspension of 1 g of 3-(4-aminobenzyl)pyridine in ethyl acetate (10 ml) at room temperature is added with stirring 1.0 ml of acetic anhydride over a 7 min period. Upon addition of the acetic anhydride (exothermic reaction) the 3-(4-aminobenzyl)pyridine goes into solution and, after 15 min, a precipitate is formed. A small portion of water (1 ml) is then added and the reaction mixture is stirred for an additional 15 min. The solution is then diluted with ethyl acetate (30 ml), benzene (30 ml) and acetone (30 ml) until the precipitate has dissolved after which the organic layer is washed with cold dilute aqueous sodium hydroxide (50 ml), saturated brine (30 ml), dried over magnesium sulfate and concentrated in vacuo to yield 1 g of product. A small amount of product is recrystallized in hexane containing a few drops of methanol to obtain the analytical sample, melting point of 153°–154° C.

TLC (silica gel GF) yields an Rf of approximately 0.30 in 7% methanol-chloroform.

The NMR (CDCl$_3$, δ) spectrum reveals peaks at 8.66, 8.58–8.33, 7.63–6.93, 3.92, and 2.13.

The mass spectrum reveals ions at m/e 226.1102, 184, 106, 183, 43, 147, 227, 39, 185, and 51.

Elemental analysis reveals: found C, 73.92; H, 6.44; and N, 12.20.

Preparation 2

N-[2-Nitro-4-(3-pyridinylmethyl)phenyl]acetamide

Refer to Chart A (conversion of A-4 to A-5).

The procedure of J. C. Howard, Org. Syn. Coll. Vol. IV, p 42 (1962) is adapted for this synthesis.

A solution of 40.93 ml of acetic anhydride and 10.5 g of N-[(3-pyridinylmethyl)phenyl]acetamide is cooled to 12° C. in an ice salt bath before 8.89 ml of 70% nitric acid was added dropwise over a 30 min period. Two exothermic events take place. The temperature rises during the nitric acid addition and again, 10–20 min after its complete addition. The temperature reaches 60° C. and then cools to ambient temperature which results in the formation of a bright yellow precipitate. The reaction mixture is poured onto 200 g of ice and made basic by the addition of 50 g of 50% aqueous sodium hydroxide. The solution is then extracted 3 times with ethyl acetate (500 ml), and the combined ethyl acetate layers are washed with saturated brine (250 ml), dried over magnesium sulfate and concentrated in vacuo to yield 14.7 g of residue. The material is chromatographed on 1250 g of regular silica gel. The column was wet-packed and eluted with 12% methanol-chloroform and fractions of 250 ml were collected. Fractions 9–13 were combined and concentrated in vacuo to yield 10.41 g of product. The product is recrystallized from methanol to produce sharp, bright orange crystals, melting point of 139°–140° C.

TLC (silica gel GF) yields an R$_f$ of approximately 0.95 in 12% methanol-chloroform.

The NMR (CDCl$_3$, δ) spectrum reveals peaks at 10.32, 8.52–8.45, 8.15–7.98, 7.65–7.18, 4.02, and 2.27.

The mass spectrum reveals ions at m/e 271.0959, 229, 43, 212, 182, 183, 181, 255, 228, and 230.

Elemental analysis reveals: found C, 61.60; H, 5.12; and N, 15.41.

Preparation 3

2-Nitro-4-(3-pyridinylmethyl)aniline

Refer to Chart a (conversion of A-5 to A-6).

The procedure of J. C. Howard, Org. Syn. Coll. Vol. IV, p 42 (1962) is adapted for this synthesis.

A mixture of 1 g of N-[2-nitro-4-(3-pyridinylmethyl)-phenyl]acetamide, water (5 ml) and 1.53 ml of 12 M hydrochloric acid is heated to reflux for 2 hr. The reaction progress is monitored by thin layer chromatography. After the disappearance of starting material the solution is poured over 20 g of ice and made basic with 50% aqueous sodium hydroxide. The solution is extracted 3 times with ethyl acetate (100 ml) and the combined ethyl acetate layers are washed with saturated brine (100 ml), dried over magnesium sulfate and concentrated in vacuo to yield 0.79 g of product. A small portion of this material is recrystalized in methanol for identification, melting point of 159° C.

TLC (silica gel GF) Rf is approximately equal to 0.46 in 7.5% methanol-chloroform.

The NMR (CDCl$_3$, δ) spectrum reveals peaks at 8.66–8.47, 8.12–7.98, 7.60–6.70, 6.33–5.90, and 3.93.

The mass spectrum reveals ions at m/e 229.0851, 182, 183, 181, 151, 230, 105, 93, 91, and 104.

Elemental analysis reveals: found C, 62.41; H, 4.84; and N, 18.03.

EXAMPLE 1

2-Hydroxymethyl-5-(3-pyridinylmethyl)benzimidazole (Formula I, Z is 3-pyridinyl, $X_1$ is —$CH_2$—, m is zero, $R_7$ is —$CH_2OH$)

Refer to Chart A (conversion of A-6 to A-8).

The procedure of M. A. Phillips, J. Chem. Soc. 2393 (1928) is adapted for this synthesis.

Part A (conversion of A-6 to A-7).

A stirred solution of 5 g of 2-nitro-4-(3-pyridinylmethyl)aniline (Preparation 3) and 2.80 ml of 20% aqueous sodium hydroxide solution in 25 ml of 95% ethanol is heated to reflux after which 5.70 g of zinc dust is added over a 10 min period. The reaction is stirred at reflux for 1.25 hr and during this time, 3 drops of 20% aqueous sodium hydroxide is added every 15 min to the mixture. Disappearance of the orange color indicates the end of the reaction. The reaction mixture is filtered warm under a nitrogen atmosphere and the filtrate quickly concentrated in vacuo to yield crude diamine residue. The diamine residue decomposes in air and, therefore, is carried quickly on to Part B.

TLC (silica gel GF) analysis yields an Rf of approximately 0.56 in 10% methanol-chloroform.

The NMR ($CDCl_3$, $\delta$) spectrum reveals peaks at 8.63–8.37, 7.60–7.07, 6.78–6.40, 3.80, and 3.27.

Part B (conversion of A-7 to A-8).

A solution of 4.34 g of diamine in 21.82 ml of 4 N hydrochloric acid and 3.32 g of glycolic acid is stirred and heated to reflux for 2 hr. The solution is cooled and poured onto 20 g of ice and made basic to pH approximately equal to 10 with concentrated ammonium hydroxide. The solution is extracted twice with ethyl acetate (150 ml) and the sides of the beaker are washed with a small amount of methanol which is also added to the ethyl acetate layer. The combined organic layers were dried over magnesium sulfate and concentrated in vacuo to yield approximately 6 g of residue. The residue is chromatographed on 800 g of regular silica gel. The column is wet-packed and eluted with 1:9 methanol-chloroform and fractions of 125 ml are collected. Fractions 46–93 are combined and concentrated in vacuo to yield 3.32 g of product. The product is recrystallized in ethyl acetate-methanol twice to yield 1.81 g of fluffy white product, melting point 159° C.

TLC (silica gel GF) Rf approximately equal to 0.46 in 12% methanol-chloroform.

The NMR (DMSO, $\delta$) spectrum reveals peaks at 8.72–8.33, 7.80–6.95, 4.70, and 4.07.

The mass spectrum reveals ions at m/e 239.1054, 220, 238, 240, 143, 221, 161, 210, 92, and 208.

Elemental analysis reveals: found C, 69.32; H, 5.70; and N, 17.26.

EXAMPLE 2

2-Formyl-5-(3-pyridinylmethyl)benzimidazole (Formula I Z is 3-pyridyl, $X_1$ is —$CH_2$—, m is zero, and $R_7$ is —CHO)

Refer to Chart A (conversion of A-8 to A-9).

A solution of 1 g of 2-hydroxymethyl-5-(3-pyridinylmethyl)benzimidazole and 10 g of activated manganese dioxide in isopropanol (20 ml) was stirred for 2 hr before another 3 g of manganese dioxide was added. The reaction mixture was stirred for an additional ½ hr, then was filtered through a pad of Celite and the solids washed with methanol (200 ml). The filtrate and washings were combined and concentrated in vacuo to yield 0.34 g of material. The manganese dioxide and Celite pad were suspended in 1 l of methanol and the mixture filtered again through a pad of Celite. The filtrate was concentrated in vacuo to yield 0.8 g of residue. The combined residues were chromatographed on 80 g of regular silica gel. The column was wet-packed and eluted with 7% methanol-chloroform and fractions of 20 ml were collected. Fractions 14 and 15 were combined to yield pure product, melting point of 187°–198° dec. with previous sintering.

A small portion of the product in methanol was treated with sodium borohydride and the resulting product was compared by thin layer chromatography with the starting alcohol. The $R_f$ of the major material of this reduction reaction appeared to be the same as the starting alcohol, indicating that the aldehyde had indeed formed.

TLC (silica gel GF) yield an $R_f$ of approximately 0.50 in 12% methanol-chloroform.

The NMR ($CD_3OD$, $\delta$) spectrum reveals peaks at 8.60–8.32, 1.83–6.88, 5.77, and 4.12; (9.93 in DMSO solution).

The mass spectrum reveals ions at m/e 237.0896, 236, 208, 238, 159, 207, 131, 181, 209, and 154.

EXAMPLE 3

5-(3-Pyridinylmethyl)benzimidazole (Formula II: Z is 3-pyridyl, $X_1$ is —$CH_2$—, m is zero, and $R_7$ is hydrogen)

Refer to Chart A (conversion of A-7 to A-8).

To a stirred solution of 0.2 g (0.84 mol) of 2-hydroxymethyl-5-(3-pyridinylmethyl)benzimidazole and 0.1 ml of saturated sodium carbonate solution in 3 ml of water at 55° C., is added 0.2 g of potassium permanganate dissolved in 3 ml of water over a 10 min period. The reaction mixture is stirred between 55°–60° C. for 1 hr after which an additional 0.1 g of potassium permanganate and 0.1 ml of sodium carbonate is added. After an additional ½ hr of heating and stirring, the reaction mixture is cooled and filtered through a pad of Celite ® and the black solid is washed with 1:3 methanol-water (100 ml). The filtrate is concentrated in vacuo to a volume approximately 7 ml after which dilute acetic acid is added to adjust the pH to 5.5. A precipitate forms which is filtered and chromatographed on a Lobar HPLC size B column. The column is eluted with 50:49:1 ethanol-ethyl acetate-acetic acid and fractions of 7 ml are collected. Fractions 26–31 are combined and concentrated in vacuo to yield approximately 60 mgs of material. Toluene is added to azeotrope the residual acetic acid which results in the formation of a white residue of titled product melting point of 155°–160° C.

TLC (silica gel GF) yields an $R_f$ of approximately 0.48 in 50:49:1 ethanol-ethyl acetate-acetic acid, and $R_f$ of approximately 0.61 in 1:1 ethanol-ethyl acetate when the compound is dissolved in pH 7 buffer; and an $R_f$ of approximately 0.36 in 12% methanol-chloroform.

The NMR ($CDCl_3 + CD_3OD$, $\delta$) spectrum reveals peaks at 8.60–8.35, 8.00, 7.72–7.03, 4.10, and 3.85.

The mass spectrum reveals ions at m/e 209, 208, 131, 147, 207, 210, 77, 78, 104, and 51.

EXAMPLE 4

5-(3-Pyridinylmethyl)benzimidazole-2-carboxylic acid, ammonium salt (Formula I: Z is 3-pyridyl, $X_1$ is —$CH_2$—, m is zero, and $R_7$ is —$COONH_4$)

Refer to Chart A (conversion of A-8 to A-11).

To a stirred, warm solution of 0.9 g of 2-hydroxymethyl-5-(3-pyridinylmethyl)benzimidazole in water (10 ml) and saturated sodium carbonate (2 ml) is added 1.34 g of potassium permangenate and an additional 20 ml of water. The reaction mixture is heated to reflux and stirred for ½ hr after which the solution is filtered hot through a pad of Celite. The residue is washed with warm water and the washings and filtrate are combined and allowed to cool to room temperature. The pH is adjusted with concentrated acetic acid to a pH of 4 and the solution is lyophilized to yield a residue which is chroamtographed on 250 g of regular silica gel. The column is wetpacked and eluted with 50:45:5 methanol-ethyl acetate-ammonium hydroxide, and fractions of 20 ml are collected. Before the compound is added to the column, approximately 1.5 l of solvent is run through the column to equilibrate the silica gel with the solvent system. Fractions 40-73 are combined and concentrated in vacuo to yield 0.61 g of crude product. Thin layer chromatography of this product in 18:21:1 methanol-ethyl acetatelammonium hydroxide reveals the pressure of two closely moving materials. Therefore, 0.136 g of this crude material is dissolved in 12 ml of warm methanol and the solution spotted for 4 preparative thin layer chromatography plates of 2 mm thickness. The plates are wetted and eluted with 18:21:1 methanol-ethyl acetate-ammonium hydroxide. Two major materials can be seen by UV, so each is individually scraped from the plate and the silica gel washed with 1:1 methanol-ethyl acetate. Each solution was concentrated in vacuo and the material with the slower $R_f$ ($R_f$ approximately equal to 0.20 in above solvent sys.) gives 50 mgs of product. The material with the greater $R_f$ is later shown to decompose as indicated by thin layer chromatography.

TLC (silica gel GF) yields an $R_f$ of approximately 0.57 in 18:21:1 methanol-ethyl acetate-ammonium hydroxide.

The IR (KBr) spectrum reveals peaks at 3600–3100 and 1645 cm$^{-1}$.

The melting point is 233°–234° C.

EXAMPLE 5

2,3-Dihydroxy-6-(3-pyridinylmethyl)quinoxaline (Formula II: Z is 3-pyridinyl, $X_1$ is —$CH_2$—)

Refer to Chart B (conversion of B-1 to B-2).

A suspension of 2 g of diamine (Example 1, part A) in diethyl oxalate (14 ml) is heated to reflux for 3 hr, after which the reaction mixture is filtered while still warm and the residual solid washed with ethyl acetate (150 ml). The filtrate and washings were combined and concentrated in vacuo to yield crude product. The residue was recrystallized from 5:90:5 water-methanol-ethanol. A large volume of solvent was required to dissolve the material and the volume of the resulting soltion was greatly reduced before cooling it for 24 hr. The resulting solid was filtered and air dried to yield 0.6 g of pure product. The product melts above 300° C. and a solvent system could not be found which would give a clear distinct spot using thin layer chromatography.

The NMR (DMSO, δ) spectrum reveals peaks at 8.66–8.42, 7.80–6.93, 4.00, and 4.00–2.6.

The mass spectrum reveals ions at m/e 253.0852, 224, 147, 254, 225, 252, 183, 196, 182, 181.

Elemental analysis reveals: found C, 65.33; H, 4.51; and N, 16.39.

FORMULAS

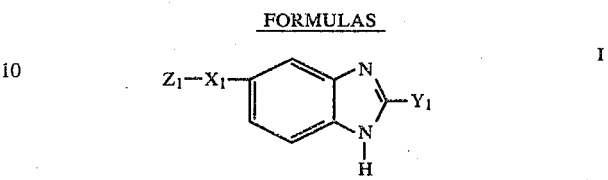

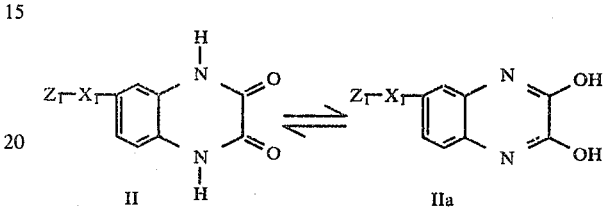

CHART A

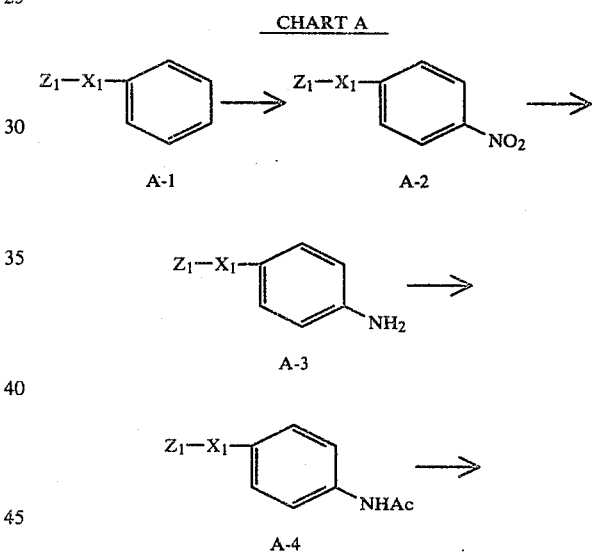

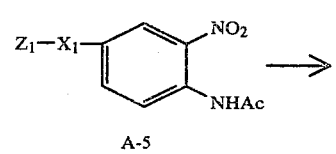

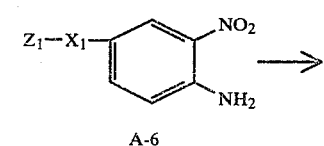

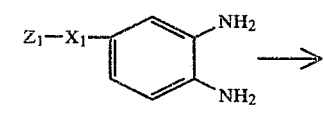

CHART A -continued

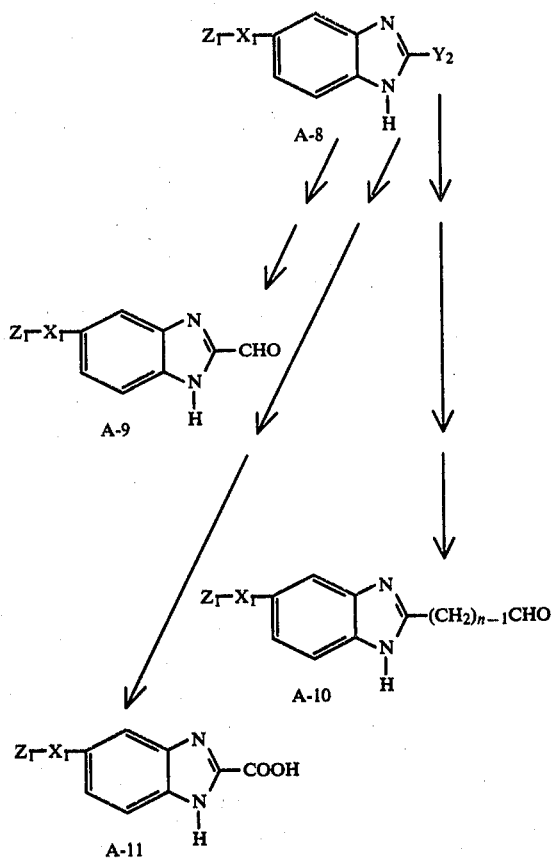

CHART B

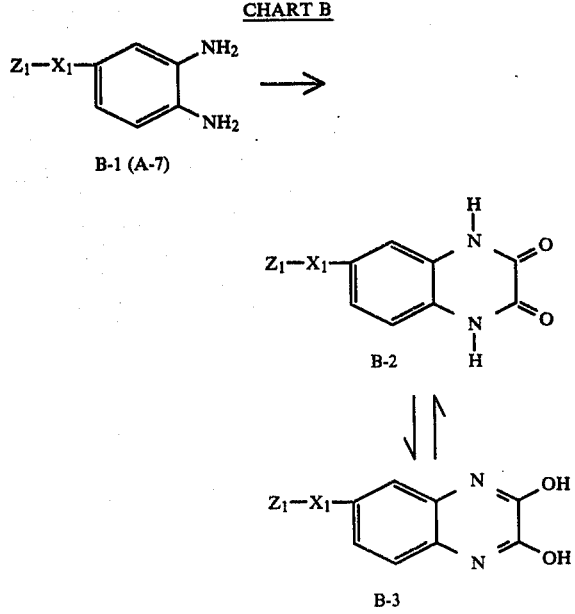

1. A compound of the formula I or II

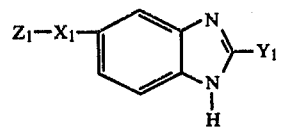

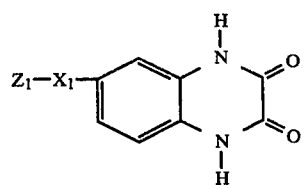

wherein $Z_1$ is
(a) 4-pyridinyl,
(b) 3-pyridinyl, or
(c) 3-pyridinyl substituted by $(C_1-C_4)$alkyl;
wherein $X_1$ is
(a) $-(CH_2)_n-$,
(b) $-O-$,
(c) $-CH_2-O-$, or
(d) $-O-CH_2-$;
wherein $Y_1$ is $-(CH_2)_m-R_7$;
wherein $R_1$ is hydrogen, a pharmacologically acceptable cation, $(C_1-C_{12})$ alkyl, $(C_3-C_{10})$ cycloalkyl, $(C_7-C_{12})$ aralkyl, phenyl, phenyl mono-, di-, or trisubstituted by chloro, or $(C_1-C_3)$ alkyl, or phenyl para-substituted by
(a) $-NHCO-R_{25}$,
(b) $-O-CO-R_{26}$,
(c) $-CO-R_{24}$,
(d) $-O-CO-(p-Ph)-R_{27}$, or
(e) $-CH=N-NH-CO-NH_2$,
wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein $-(p-Ph)$ is 1,4-phenylene;
wherein $R_7$ is
(a) $-CH_2OH$,
(b) $-CHO$, or
(c) $-COOR_1$;
wherein m is an integer of from 0 to 4; and n is an integer of from 1 to 3, inclusive;
including, pharmacologically acceptable acid addition salts thereof, and tautomeric forms thereof.

2. A compound of claim 1 of the formula I, wherein $Y_1$ is $-(CH_2)_mR_7$, m is zero, $X_1$ is $-(CH_2)_n$ wherein n is one, or $-O-$, $Z_1$ is 3-pyridinyl, and $R_7$ is $-COOR_1$, $-CH_2OH$, or $-CHO$.

3. 2-Hydroxymethyl-5-(3-pyridinylmethyl)benzimidazole, a compound of claim 2.

4. 2-Formyl-5-(3-pyridinylmethyl)benzimidazole, a compound of claim 2.

5. A compound of claim 2, wherein $X_1$ is $-CH_2-$ and $R_7$ is $-COOR_1$.

6. 2,3-Dihydroxy-6-(3-pyridinylmethyl)quinoxaline, a compound of claim 1.

7. 5-(3-Pyridinylmethyl)benzimidazole-2-carboxylic acid, ammonium salt, a compound of claim 2.

* * * * *